(12) United States Patent
Lo Presti et al.

(10) Patent No.: US 10,293,051 B2
(45) Date of Patent: May 21, 2019

(54) FGF-18 FORMULATION IN XYLOGLUCAN GELS

(71) Applicant: ARES TRADING S.A., Aubonne (CH)

(72) Inventors: Caterina Lo Presti, Rome (IT); Donatella Bulone, Palermo (IT); Clelia Dispenza, Palermo (IT)

(73) Assignee: ARES TRADING S.A., Aubonne (CH)

(*) Notice: Subject to any disclaimer, the term of this patent is extended or adjusted under 35 U.S.C. 154(b) by 3 days.

(21) Appl. No.: 15/105,622

(22) PCT Filed: Dec. 23, 2014

(86) PCT No.: PCT/EP2014/079194
§ 371 (c)(1),
(2) Date: Jun. 17, 2016

(87) PCT Pub. No.: WO2015/097233
PCT Pub. Date: Jul. 2, 2015

(65) Prior Publication Data
US 2016/0317668 A1    Nov. 3, 2016

(30) Foreign Application Priority Data

Dec. 23, 2014 (EP) .................................. 13199588

(51) Int. Cl.
| | | |
|---|---|---|
| A61K 47/36 | (2006.01) |
| A61K 47/02 | (2006.01) |
| A61K 38/18 | (2006.01) |
| A61L 27/52 | (2006.01) |
| A61K 9/00 | (2006.01) |
| A61L 27/54 | (2006.01) |

(52) U.S. Cl.
CPC ............ A61K 47/36 (2013.01); A61K 9/0019 (2013.01); A61K 9/0024 (2013.01); A61K 38/1825 (2013.01); A61K 47/02 (2013.01); A61L 27/52 (2013.01); A61L 27/54 (2013.01); A61L 2300/414 (2013.01); A61L 2430/06 (2013.01)

(58) Field of Classification Search
None
See application file for complete search history.

(56) References Cited

U.S. PATENT DOCUMENTS

| | | | |
|---|---|---|---|
| 6,245,354 B1 * | 6/2001 | Miyazaki ................ | A61K 9/02 424/400 |
| 2005/0043813 A1 | 2/2005 | Kusanagi et al. | |
| 2008/0193425 A1 | 8/2008 | Ellsworth | |
| 2010/0016223 A1 | 1/2010 | Gimona et al. | |
| 2016/0303291 A1 | 10/2016 | Canal et al. | |

FOREIGN PATENT DOCUMENTS

| | | | |
|---|---|---|---|
| CN | 102600066 | | 7/2012 |
| WO | WO 2014/062538 | * | 4/2014 |
| WO | WO 2015/097236 | | 7/2015 |

OTHER PUBLICATIONS

Gerwin N, Hops C, Lucke A. Intraarticular drug delivery in osteoarthritis. Adv Drug Deliv Rev. 2006 20, 2006;58(2):226-42. Epub Feb. 23, 2006.*
Shirakawa et al. Tailoring of xyloglucan properties using an enzyme. Food Hydrocolloids, vol. 12, Issue 1, 1998, pp. 25-28.*
Madan, M. et al. "In Situ Forming Polymeric Drug Delivery Systems" *Indian Journal of Pharmaceutical Sciences*, May 2009, pp. 242-251, vol. 71, No. 3.
Written Opinion in International Application No. PCT/EP2014/079194, dated Apr. 20, 2015, pp. 1-7.

* cited by examiner

*Primary Examiner* — Marianne P Allen
(74) *Attorney, Agent, or Firm* — Saliwanchik, Lloyd & Eisenschenk

(57) ABSTRACT

The invention relates to the field of pharmaceutical formulations. More particularly, it is directed to xyloglucan hydrogels comprising Fibroblast Growth Factor 18 (FGF-18) compounds and methods of producing such hydrogels. The hydrogels of the invention can be used, once formed in situ, for the treatment of cartilage disorders such as osteoarthritis or cartilage injury.

11 Claims, 12 Drawing Sheets
Specification includes a Sequence Listing.

(a)                            (b)

SEQ ID NO:1 (human FGF-18)

MYSAPSACTCLCLHFLLLCFQVQVLVAEENVDFRIHVENQTRARDDVSRKQLRLYQLYSRTSGKHIQVLGRRISARGEDGDK
YAQLLVETDTFGSQVRIKGKETEFYLCMNRKGKLVGKPDGTSKECVFIEKVLENNYTALMSAKYSGWYVGFTKKGRPRKGPK
TRENQQDVHFMKRYPKGQPELQKPFKYTTVTKRSRRIRPTHPA

Figure 17 a

SEQ ID NO:2 (sprifermin)

MEENVDFRIHVENQTRARDDVSRKQLRLYQLYSRTSGKHIQVLGRRISARGEDGDKYAQLLVETDTFGSQVRIKGKETEFYL
CMNRKGKLVGKPDGTSKECVFIEKVLENNYTALMSAKYSGWYVGFTKKGRPRKGPKTRENQQDVHFMKRYPKGQPELQKPFK
YTTVTK

Figure 17 b

FGF-18 FORMULATION IN XYLOGLUCAN GELS

CROSS-REFERENCE TO RELATED APPLICATION

This application is the U.S. national stage application of International Patent Application No. PCT/EP2014/079194, filed Dec. 23, 2014.

The Sequence Listing for this application is labeled "Seq-List.txt" which was created on Jun. 15, 2016 and is 4 KB. The entire content of the sequence listing is incorporated herein by reference in its entirety.

FIELD OF INVENTION

The invention relates to the field of pharmaceutical formulations. More particularly it is directed to Fibroblast Growth Factor 18 (FGF-18) protein formulation in xyloglucan gels and to methods of producing such formulations.

BACKGROUND OF THE INVENTION

Fibroblast Growth Factor 18 (FGF-18) is a member of the Fibroblast Growth Factor (FGF) family of proteins, closely related to FGF-8 and FGF-17. Members of the FGF family are characterized by heparin-binding domains. Such a putative heparin-binding domain has been identified for FGF-18. It is postulated that receptor-mediated signaling is initiated upon binding of FGF ligands complexed with cell-surface heparin sulfate proteoglycans.

It has been shown that FGF-18 is a proliferative agent for chondrocytes and osteoblasts (Ellsworth et al., 2002; Shimoaka et al., 2002). FGF-18 has been proposed for the treatment of cartilage disorders such as osteoarthritis (OA) and cartilage injury (CI), either alone (WO2008/023063) or in combination with hyaluronic acid (WO2004/032849).

Pharmaceutical compositions comprising an FGF polypeptide are known from the art. WO2012/172072 describes a freeze-dried formulation containing FGF-18, wherein said composition comprises FGF-18, a buffer, a poloxamer surfactant and a sugar as stabilizing agent. Said FGF-18 freeze-dried formulation is showing promising results in the treatment of OA or CI. The current dosing regimen, using said freeze-dried formulation, is a treatment cycle of once weekly injection for 3 weeks. The treatment cycle can be repeated.

In the case of CI, the main drawback of the current formulation is that, once injected intraarticularly (i.a.), the presence of FGF-18 in the synovial fluid may also induce uncontrolled cartilage growth in healthy areas. This can, of course, induce unwanted effects such as reduced joint mobility. The delivery of FGF-18 selectively at the level of the target site could promote the cartilage growth only in the damaged area. In particular, the delivery of FGF-18 at the level of the damaged area could be highly beneficial for the treatment of CI coupled with microfracture techniques. Microfracture is an articular cartilage repair surgical technique that works by creating small fractures in the underlying bone. This causes the release of pluripotent mesenchymal stem cells from the bone marrow (Ringe, J. et al., 2012). Filling the cartilage hole with an injectable gel containing FGF-18 would direct cells within the gel that would then act as mechanical supports for cell growth and drug reservoirs at the same time. For this reason, it would be preferable if FGF-18 is not released from the gel but it stays entrapped in the matrix.

A typical approach in tissue engineering is the confinement of growth factors in a 3D matrix, i.e., a scaffold, that can be either implanted or injected, depending on the mechanical properties, in order to assume the shape of the acceptor site. Mandatory characteristics of the scaffold are biocompatibility and resorbability. Additionally, scaffolds must be able to provide cells the ideal environment to grow, proliferate and reform the damaged tissue. Ideally, the matrix should resemble the same mechanical properties as the original tissue and should present a microporosity able to host cells (interconnected pores with a sufficient size) (Tessmar and Göpferich, 2007).

Hydrogels are three-dimensional networks of hydrophilic polymer chains able to absorb and retain large amounts of water. Their main feature is that they are able to swell or shrink but not dissolve in aqueous media. Therefore, it is possible to entrap in their matrix an active molecule (Active Pharmaceutical Ingredient, i.e., API) that is then slowly released or retained, depending on the presence of specific interactions between the matrix and the API (Lo Presti et al., 2011). The advantage of the use of injectable hydrogels for treating a cartilage disorder is the possibility to inject the scaffold by arthroscopy in the cartilage defect, without the need of any invasive surgery making use of solid scaffolds.

Among the diverse hydrogels that are already known, some formulations are based on polymers able to undergo the gelling process in response to a particular physical or chemical stimulus. These are present as viscous injectable liquids that, once injected, turn to macroscopic gels in response to environmental stimuli at the site of injection, such as changes in temperature, pH or ionic strength. The composition of the formulation can be tuned in order to obtain hydrogels with different characteristics, such as viscoelastic properties, microporosity, etc. (WO2008/063418; Lo Presti et al., 2001; C. Dispenza et al., 2011).

Hydrogels of natural polymers, particularly polysaccharides, have been widely used for their unique advantages, such as nontoxicity, biocompatibility, biodegradability, and abundance. Natural polymers including collagen, gelatin, glycosaminoglycans, and derivatives thereof often possess a high affinity for proteins. A large number of biopolymers possess the property to self-structure upon temperature or ionic variation.

Xyloglucans are a major class of structural polysaccharides found in the primary cell walls of higher plants. When xyloglucan is partially degalactosylated (Deg-XG), it becomes temperature-responsive (thermosensitive): it can form physical, reversible gels with temperature variations in aqueous solutions. Degalactosylation of xyloglucan is achieved with β-galactosidase (Rilton et al., 2011). Degalatosylated xyloglucans present some advantages over other currently available in-situ gelling systems: the gelation does not require the presence of divalent cations and it is not affected by the charged nature of the drug; the gel forms in few minutes, depending on the concentration of polymer in solution and temperature (Shirakawa et al., 1998).

When preparing a pharmaceutical composition comprising a bioactive protein, said composition must be formulated in such a way that the activity of the protein is maintained for an appropriate period of time. A loss in activity/stability of the protein may result from chemical or physical instabilities of the protein, notably due to denaturation, aggregation or oxidation. The resulting products may thus be pharmaceutically unacceptable. Although the use of excipient(s) and/or hydrogels is known to increase the stability of a given protein, the stabilizing effects of these excipients is highly dependent on the polymer in the gels, the nature of the excipients and the bioactive protein itself.

There remains a need for further formulations containing FGF-18 as an active ingredient, wherein said formulations, while keeping the bioactivity of the active ingredient and being suitable for use in injection, preferably for intra-articular injection, allow reduction of the number of injections needed for the treatment. Such a characteristic would allow the reduction of the risk of infections and would increase the patient's convenience. Said formulations could be useful for administration to a patient for the treatment of a cartilage disorder, such as osteoarthritis or cartilage injury.

SUMMARY OF THE INVENTION

It is an object of the present invention to provide a novel formulation containing an FGF-18 protein. More particularly, said formulation is a hydrogel containing FGF-18, wherein the hydrogel is preferably a thermosensitive hydrogel, and more preferably a xyloglucan gel. The invention also provides methods for preparing the hydrogels according to the present invention, starting from a liquid formulation. The hydrogel containing FGF-18, herein described, may be useful for administration in the treatment of cartilage disorders, such as osteoarthritis or cartilage injury. Of particular interest is a xyloglucan hydrogel, further containing FGF-18 protein. It is noted that before injection, or before being submitted to a gelling temperature, the hydrogels according to the invention are in liquid form.

In a first aspect, the invention provides a liquid formulation comprising or consisting of xyloglucan, a buffer and FGF-18 as active ingredient. This formulation is provided as a gelation system, being in a liquid form when stored at 5° C. and becoming a gel (or a hydrogel) at 37° C., i.e. once injected in the human body. Preferably, the xyloglucan is a degalactosylated xyloglucan, even more preferably a Deg-xyloglucan having a degalactosylation degree of or about 44 or 45%, and the buffer is a phosphate buffer, such as PBS. In a preferred embodiment, the concentration of xyloglucan is at or about 1 to 5% wt, preferably at or about 3 to 4% wt or even more preferably at or about 4%, the buffer is in a concentration at or about 95 to 99% wt, preferably at or about 96% wt. Preferably, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined hereafter.

In a second aspect, the invention provides a method for preparing the hydrogel of FGF-18, comprising the steps of:
1) preparing a solution comprising or consisting of FGF-18, together with xyloglucan and a buffer, and
2) exposing the gel at a temperature of 37° C. or about 37° C. to form the gel,
wherein the xyloglucan is preferably a degalactosylated xyloglucan, even more preferably a Deg-xyloglucan having a degalactosylation degree of or about 44 or 45%, and the buffer is a phosphate buffer, such as PBS. Preferably, the pH of the final formulation is kept at or about 5 to 8, more particularly at or about 5.5 to 7.5, such as at or about 5.5, 6, 6.5, 7, 7.3 or 7.5, and even more preferably at or about 5.5 to 6. In a preferred embodiment, FGF-18 is selected from the group consisting of: 1) a polypeptide comprising or consist-ing of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined hereafter. In a preferred embodiment, the gel is submitted to the gelling temperature upon injection in the human body, i.e., in situ.

In a third aspect, the invention provides a hydrogel obtained by the method according to the second aspect.

In a fourth aspect, the invention provides an article of manufacture for pharmaceutical or veterinary use, comprising a container comprising xyloglucan, FGF-18 protein and a buffer, wherein the xyloglucan is preferably a degalactosylated xyloglucan, even more preferably a Deg-xyloglucan having a degalactosylation degree of or about 44 or 45%, and the buffer is a phosphate buffer, such as PBS. Preferably, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined hereafter.

Definitions

The term "FGF-18 protein" or "FGF-18", as used herein, is intended to be a protein maintaining at least one biological activity of the human FGF-18 protein. FGF-18 may be native, in its mature form, or a truncated form thereof. Biological activities of the human FGF-18 protein include, notably, the increase of osteoblastic activity (see WO98/16644) or cartilage formation (see WO2008/023063).

Native, or wild-type, human FGF-18 is a protein expressed by chondrocytes of articular cartilage. Human FGF-18 was first designated zFGF-5 and is fully described in WO98/16644. SEQ ID NO: 1 corresponds to the amino acid sequence of the native human FGF-18, with a signal peptide consisting of amino acid residues 1(Met) to 27(Ala). The mature form of human FGF-18 corresponds to the amino acid sequence from residue 28 (Glu) to residue 207 (Ala) of SEQ ID NO: 1 (180 amino acids).

FGF-18, in the present invention, may be produced by a recombinant method, such as taught by WO2006/063362. Depending on the expression systems and conditions, FGF-18 in the present invention is expressed in a recombinant host cell with a starting Methionine (Met residue) or with a signal sequence for secretion. When expressed in a prokaryotic host, such as in *E. coli*, FGF-18 contains an additional Met residue in the N-terminal of its sequence. For instance, the amino acid sequence of human FGF-18, when expressed in *E. coli*, starts with a Met residue in N-term (position 1) followed by residues 28 (Glu) to residue 207 (Ala) of SEQ ID NO: 1.

The term "truncated form" of FGF-18, as used herein, refers to a protein which comprises or consists of residues 28 (Glu) to 196 (Lys) of SEQ ID NO: 1. Preferably, the truncated form of FGF-18 protein is the polypeptide designated "trFGF-18" (170 amino acids), which starts with a Met residue (in the N-terminal) followed by amino acid residues 28 (Glu)-196 (Lys) of the wild-type human FGF-18. The amino acid sequence of trFGF-18 is shown in SEQ ID NO: 2 (amino acid residues 2 to 170 of SEQ ID NO: 2 correspond to amino acid residues 28 to 196 of SEQ ID NO: 1). trFGF-18 is a recombinant truncated form of human FGF-18, produced in *E. coli* (see WO2006/063362). The International Nonproprietary Name (INN) for this particular form of FGF-18 is sprifermin. Sprifermin has been shown to display similar activities to the mature human FGF-18, e.g., it increases chondrocyte proliferation and cartilage deposition, leading to repair and reconstruction of a variety of cartilaginous tissues (see WO2008/023063).

The terms "active molecule" or "active ingredient" relate to an Active Pharmaceutical Ingredient, i.e., API. The preferred API, in the context of the present invention, is FGF-18.

The term "gel" or "hydrogel" is used interchangeably in this application. They refer to a 3D matrix, or scaffold, useful as a pharmaceutical formulation.

The term "liquid formulation" as used herein refers to the hydrogel formulation before injection, as the gel itself forms only upon temperature variation, once administered in the human body.

The term "xyloglucan" refers to any form of xyloglucan, i.e., a hemicellose produced in the primary cell wall of vascular plants. It is a well-known gelating agent, notably when submitted to a temperature of about 37° C. One of the preferred forms that can be used in the context of the present invention is a degalactosylated form, more preferably having a degree of degalactosylation of or about 44 or 45%. Degalactosylated xyloglucan is reported here as Deg-Xyloglucan, D-xyloglucan, or Deg-XG.

The term "buffer", as used herein, refers to solutions of compounds that are known to be safe in formulations for pharmaceutical or veterinary use and that have the effect of maintaining or controlling the pH of the formulation in the pH range desired for the formulation. Acceptable buffers for controlling pH at a moderately acidic pH to a moderately basic pH include, but are not limited to, phosphate, acetate, citrate, arginine, TRIS, and histidine buffers. "TRIS" refers to 2-amino-2-hydroxymethyl-1,3,-propanediol, and to any pharmacologically acceptable salt thereof. A preferred buffer according to the present invention is a phosphate buffer, such as PBS.

The term "vial" or "container", as used herein, refers broadly to a reservoir suitable for retaining the formulation in a liquid form. Examples of a vial that can be used in the present invention include syringes, ampoules, cartridges, or other such reservoirs suitable for delivery of the FGF-18 formulation to the patient via injection, preferably via intra-articular injection. Vials suitable for packaging products for intra-articular administration are well-known and recognized in the art.

The term "cartilage disorder", as used herein, encompasses disorders resulting from damage due to traumatic injury or chondropathy. Examples of cartilage disorders that may be treated by the administration of the FGF-18 formulation described herein include, but are not restricted to, arthritis, such as osteoarthritis or rheumatoid arthritis, and cartilage injury.

The term "osteoarthritis" is used to intend the most common form of arthritis. It may be caused by the breakdown of cartilage. Bits of cartilage may break off and cause pain and swelling in the joints between bones. Over time the cartilage may wear away entirely, and the bones will rub together. Osteoarthritis can affect any joint but usually concerns the hands and weight-bearing joints such as the hips, knees, feet, and spine. In a preferred example, the osteoarthritis may be knee osteoarthritis or hip osteoarthritis. The skilled person is fully aware of osteoarthritis classifications that are used in the art, in particular the OARSI assessment system (see, for instance, Custers et al., 2007). Osteoarthritis is one of the preferred cartilage disorders that can be treated by administering the FGF-18 formulations according to the present invention.

The term "cartilage injury" as used herein is a cartilage disorder or cartilage damage resulting notably from a trauma. Cartilage injuries can occur as a result of traumatic mechanical destruction, notably further to an accident or surgery. Also considered within this definition is sport-related injury or sport-related wear of tissues of the joint.

The term "µg" or "mcg" is used interchangeably and refer to a division of the SI unit for mass.

DETAILED DESCRIPTION OF THE INVENTION

The main object of the present invention is a xyloglucan gel formulation (or hydrogel) comprising or consisting of a xyloglucan, an FGF-18 protein and a buffer. Said hydrogel being in a liquid form before injection in situ, or before being exposed to the gelling temperature, the alternative main object of the invention is a xyloglucan liquid formulation comprising or consisting of a xyloglucan, an FGF-18 protein and a buffer. In a preferred embodiment, the xyloglucan is a degalactosylated xyloglucan, even more preferably a Deg-xyloglucan having a degalactosylation degree of or about 44 or 45%, and the buffer is a phosphate buffer, such as PBS.

Said liquid formulation (or hydrogel) is suitable for injection at the cartilage level. Preferably, the FGF-18 protein is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1 and 3) a polypeptide comprising or consisting of SEQ ID NO: 2. More preferably, FGF-18 is sprifermin.

The advantage of the use of injectable hydrogels is the possibility to inject the scaffold (or the component of the scaffold, said scaffold being in liquid form before being exposed to the gelling temperature), already containing FGF-18, in the cartilage defect, without the need of any invasive surgery making use of solid scaffolds. Preferably, the injection is done by arthroscopy.

Most preferably, the hydrogels according to the present invention are formed in situ, upon injection.

In a preferred embodiment, the present invention is directed to the use of liquid polymeric solutions (or liquid formulations) able to undergo a gelation process, once administered to the patient, due to temperature variations.

It is noted that liquid formulation and hydrogel, in the context of this invention, refer to the same formulation. However, liquid formulation is particularly directed to the form of the formulation before gelation, whereas hydrogel refers to the same formulation, but having been submitted to gelation process. The components of both formulations are thus the same.

The concentration of FGF-18 in the liquid formulation (or in the hydrogel) is preferably at or about 1 ng/mL to 600 mcg/mL, preferably at or about 0.001, 0.006, 0.01, 0.1, 1, 5, 6.5, 10, 20, 30, 40, 50, 54, 60, 70, 80, 90, 100, 150, 200, 250, 300, or 540 mcg/mL. More preferably FGF-18 is at a concentration at or about 0.1 to 100 mcg/mL, even more preferably at or about 0.1 to 54 mcg/mL.

The gelation component, i.e., xyloglucan, in the liquid formulation or in the hydrogel, is at a concentration at or about 1 to 5% wt, preferably at or about 2 to 4% wt, even preferably at or about 3 or 4% wt. Preferably, said xyloglucan is a degalactosylated xyloglucan, and even more preferably, said Deg-xyloglucan has a degalactosylation degree of or about 44 or 45%. The particular advantage of said Deg-xyloglucan is that the transition soluble-gel is at around 37° C., i.e., the temperature of the human body, whereas the transition gel-sol is at around 70° C. Therefore, once the gel is formed in the human body, it remains in the gel state; there is no risk it returns into the soluble state.

The buffer, such as PBS, is at or about 95-99% wt, more preferably at or about 96-97% wt.

In a preferred embodiment, the liquid formulation or the hydrogel (as the liquid formulation forms a hydrogel once injected in the human body) comprising or consisting of FGF-18 at or about 0.1-100 mcg/mL, xyloglucan at 3 or 4% wt, the buffer at 96 or 97% wt. Preferably the ratio between the polymer (i.e., xyloglucan) and FGF-18 is between 20:1 and 1:1, more preferably 9:1.

Once mixed together, the final concentrations of each component are preferably as follows:
FGF-18: from 0.00001 to 0.6 wt %, such as 0.0054 wt %;
Xyloglucan: from 1 to 5 wt %, such as 3 or 4 wt %; and
Buffer: from 95 to 99% wt, such as 96 or 97% wt.

In a preferred embodiment, the pH of the final formulation is kept at or about 5 to 8, more particularly at or about 5.5 to 7, such as at or about 5.5, 6, 6.5, 7, 7.3 or 7.5, and even more preferably at or about 5.5 to 6.

The invention further provides a method for preparing the hydrogels of FGF-18, comprising the steps of:
1) preparing a liquid formulation comprising or consisting of FGF-18, together with xyloglucan and a buffer, and
2) exposing the gel to a temperature of 37° C. or about 37° C. to form the gel,
wherein the xyloglucan is preferably a degalactosylated xyloglucan, even more preferably a Deg-xyloglucan having a degalactosylation degree at or about 44 or 45%, and the buffer is a phosphate buffer, such as PBS. Preferably the pH of the final formulation is kept at or about 5 to 8, more particularly at or about 5.5 to 7, such as at or about 5.5, 6, 6.5, 7, 7.3 or 7.5, and even more preferably at or about 5.5 to 6. In a preferred embodiment, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined hereafter. In a preferred embodiment, the liquid formulation is submitted to the gelling temperature upon injection in the human body, i.e., in situ, hence forming a gel (or hydrogel).

Preferably the ratio between the polymer (i.e., xyloglucan) and FGF-18 is between 20:1 and 1:1, more preferably 9:1. Each of the compounds (i.e., FGF-18, xyloglucan and the buffer) can be used according to any one of the concentrations, pHs, and/or ratios above described.

In a third aspect, the invention provides an article of manufacture for pharmaceutical or veterinary use, comprising a container comprising or consisting the liquid formulation according to the invention. Said liquid formulation comprises or consists of a xyloglucan, an FGF-18 protein, and a buffer, wherein the xyloglucan is preferably a degalactosylated xyloglucan, even more preferably a Deg-xyloglucan having a degalactosylation degree of or about 44 or 45%, and the buffer is a phosphate buffer, such as PBS. Preferably, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1 and 3) a polypeptide comprising or consisting of SEQ ID NO: 2. More preferably, FGF-18 is sprifermin, as defined hereafter. Preferably the ratio between the polymer (i.e. xyloglucan) and FGF-18 is between 20:1 and 1:1, more preferably 9:1. Each of the compounds (i.e., FGF-18, xyloglucan and the buffer) can be used according to any one of the concentrations disclosed herein.

The present invention is further directed to a hydrogel obtained according to the method described above.

Also described is a packaging material providing instructions to form the hydrogel according to the present invention, preferably in situ.

The liquid formulation capable of forming the hydrogel of the invention may be stored for at least about 12 months to about 24 months. Under preferred storage conditions, before the first use, the formulations are kept away from bright light (preferably in the dark), preferably at refrigerated temperature (at or about 2-8° C.).

The present invention provides liquid formulations or hydrogels comprising FGF-18, in particular for single use, suitable for pharmaceutical or veterinary use. The liquid formulations or hydrogels (as the liquid formulations are capable of forming a hydrogel when exposed to a gelling temperature) comprising FGF-18, according to the present invention, can be used for administration for improving cartilage repair or for the treatment of cartilage disorders, such as osteoarthritis or cartilage injuries.

These liquid formulations, or hydrogels, are suitable for use in injection and alternative delivery systems. In a particularly preferred embodiment, the formulations of the invention are for intra-articular injection. They can be administered by direct injection into the defect, wherein the gel is preferably formed in situ. In a preferred embodiment of the present invention, the intraarticular administration is done in a joint selected from the joint of the hip, knee, elbow, wrist, ankle, spine, foot, finger, toe, hand, shoulder, rib, shoulder blade, thigh, shin, heel and along the bony points of the spine. In yet another preferred embodiment the intra-articular administration is done in the joint of the hip or the knee.

The following examples are provided to further illustrate the preparation of the liquid formulations and hydrogels of the invention. The scope of the invention shall not be construed as merely consisting of the following examples.

DESCRIPTION OF THE FIGURES

FIG. 17: Sequence of human FGF-18, corresponding to SEQ ID NO: 1 (a) and sequence of sprifermin corresponding to SEQ ID NO: 2 (b).

DESCRIPTION OF THE SEQUENCES

Figure 1:
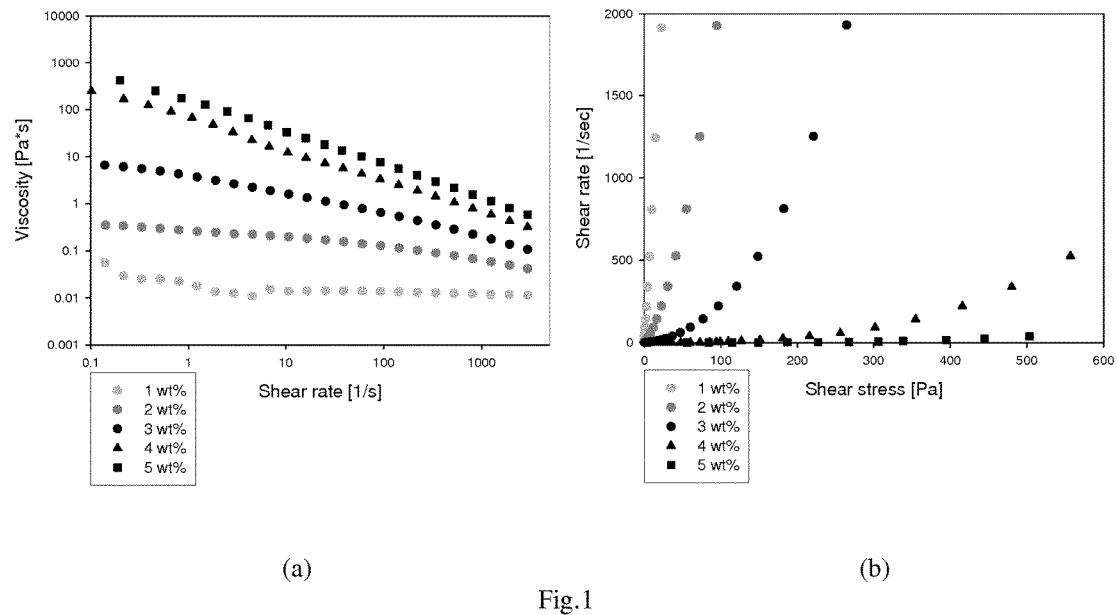
FIG. 1: (a) Shear viscosity against shear rate and (b) shear rate against shear stress for Deg-XG systems prepared in water.

SEQ ID NO: 1: Amino acid sequence of the native human FGF-18.

SEQ ID NO: 2: Amino acid sequence of the recombinant truncated FGF-18 (trFGF-18 or sprifermin).

EXAMPLES

Materials

The recombinant truncated FGF-18 (trFGF-18 or sprifermin) of the present examples has been prepared in house by expression in *E. coli*, according to the technique described in WO2006/063362. In the following examples, sprifermin and FGF-18 are used interchangeably.

Other main substances used in the examples are the following:
Xyloglucan from Tamarind seeds was obtained from Megazyme International (Ireland). It was degalactosylated according to a protocol reported by Rilton et al., 2011.
BSA, HSA and Poloxamer F68 were obtained from Sigma-Aldrich.
Penicillin Streptomycin (Pen-Strep) and Dulbecco PBS 10× were obtained from Gibco.
Chitosan 75% DD HMW, Sigma-Aldrich 419419.
Chitosan 95% DD LMW, Faravelli 43000.
Chitosan 95% DD HMW, Heppe medical 24711.

Qualitative characterizations were performed on solutions of a degalactosylated variant of xyloglucan (Deg-XG) in order to perform an initial rapid screening of different formulations. In particular, these characterizations were syringability tests at room temperature and tilting behavior tests at 37° C. On selected systems further characterizations and experimentations were also performed, also in the presence of FGF-18 as appropriate.

In order to distinguish clearly in this section between the formulation before and after the gelation process, the former has been referred to as "liquid solution" and the latter as "gel".

Methods

Preparation of FGF-18 Solutions

FGF-18 at 5.41 mg/ml is stored at −80° C. in individual 3 ml vials and, after melting at room temperature, it is either directly added to the polymer solution (at a 9:1 ratio between the polymer solution and FGF-18) to attain the target final concentration of 540 mcg/ml or diluted with the "protein bulk" to attain the target final concentration of 54 mcg/ml prior to the addition to the polymer solution. "Protein bulk" is a PBS solution at pH 7.3 prepared from $Na_2HPO_4$ (7 mM), $KH_2PO_4$ (1 mM) and KCl (2.7 mM). Ionic strength of this buffer is about 25 mM.

Preparation of Polymers' Solvents and Release Media (Modified Mock Synovial Fluids)

Type I (also named D-PBS): Dulbecco PBS 10×, ten times diluted with Millipore water, 0.1 wt % Pen-Strep; pH 5.5. D-PBS 1× ionic strength is about 166 mM and its composition is as follows: $CaCl_2$ (0.9 mM), $MgCl_2$ (0.49 mM), KCl (2.66 mM), $KH_2PO_4$ (1.47 mM), NaCl (137.9 mM), $Na_2HPO_4$ (8.06 mM).

Type II: as Type I with 0.1 wt % BSA.

Type III: as the "protein bulk" with 0.25 g/L Poloxamer, 1 wt % Pen-Strep and 1 wt % HSA; pH 7.3.

FGF-18 Loading Protocol

For Deg-XG solutions, prepared in Type I solvent (D-PBS) or PBS pH 7.3 (prepared as the "protein bulk"), polymer concentration was incremented by 10% in order to have the same final polymer concentration as when systems are loaded with FGF-18 solutions at a weight ratio 9:1.

The protein solution was slowly charged with a syringe, with the needle shuffling around in the sample to ensure a uniform distribution. The loaded gel was always stored at 5° C., overnight, without stirring before use.

Polymer Solutions: Preparation and Storage

Deg-XG solutions were prepared both in Millipore water and in Type I solvent, pH 5.5. Deg-XG solution at 4.4 wt % was also prepared in the "protein bulk", at pH 7.3.

The dissolution procedure is as follows:
Addition of solid polymer to cold water or cold PBS at the desired concentration;

Homogenization for 5 h at 5° C. and 13500 rpm;
Autoclaving at 120° C. for 20 minutes; and
Storage at 5° C.

During the pre-formulation work, chitosan was mixed with other excipients in order to obtain aqueous solutions with an acceptable osmolality for i.a. injections (target: 350 mOsm/Kg). The liquid solutions were then tested for their gelation time and temperature.

Syringability, Shear Viscosity and Tilting Behavior Tests
Syringability:
Syringability was tested at room temperature by injecting 1 ml through a syringe with a G25 needle. Injection time and the residual amount in the syringe were evaluated.
Shear Viscosity:
Shear viscosity measurements were made at 25° C. with an Ar 1000 rheometer (TA Instruments).
Tilting Behavior Tests:
2-3 ml of solution were incubated at 37° C. in transparent cylindrical tubes and observed after different times. Tubes were tilted to assess if the material was liquid-like ("flow") or gel-like ("no flow").
Dynamic-Mechanical Stress Rheometry
Dynamic-mechanical properties of Deg-XG gels were assessed by small-amplitude shear experiments (stress controlled). Tests were performed using a stress-controlled Ar 1000 rheometer (TA Instruments) with an acrylic plate geometry (diam. 4 cm) and a gap of 500 μm.
Strain sweep tests were performed at 1 Hz frequency, while frequency sweep tests were performed at $4 \cdot 10^{-3}$ strain. Strain sweep and frequency sweep tests were both performed after 5 and 30 minutes of incubation at 37° C.
Gelation kinetics at 37° C. were studied with repeated frequency sweep tests at $4 \cdot 10^{-3}$ strain.
Gelation kinetics at 25° C. were studied with time sweep tests at a fixed frequency of 1 Hz and strain of $4 \cdot 10^{-3}$.
SEM Microscopy
Surface morphology was imaged by a field emission scanning electron microscopy (FESEM) system (JEOL) at an accelerating voltage of 10 kV. Samples for FESEM were coated with a gold layer by JFC-1300 gold coater (JEOL) for 50 s at 30 mA before scanning. Freeze-dried samples were mounted on SEM aluminium stubs by means of a graphite adhesive layer.
Swelling-Erosion Studies
For preliminary studies with Deg-XG gels prepared in water, gel samples (4-6 for each system) were put onto pre-weighed cylindrical glass vials with a porous bottom (sintered glass of porosity G0/G1), immersed in a large excess of release medium type I and placed in a thermostat set at 37° C. For Deg-XG gels loaded with FGF-18, gel samples were put onto the pre-weighed inserts of a multi-well plate with a porous membrane (0.4 μm) on the bottom, immersed in the release medium type II and placed in a thermostat set at 37° C. Orbital shaking at 100 rpm was provided. Release medium was changed every 2-3 days. Gel samples were weighed before incubation and after different times of incubation at 37° C. Ws(t) is the weight of the swollen sample at the time t and Ws(0) is the weight of the sample at time=0.
Erosion-Release Studies
For the release study, performed on 4 wt % Deg-XG prepared in PBS at pH 7.3 (as the "protein bulk") and loaded with FGF-18, gel samples were put onto the pre-weighed inserts of multi-well plates with a porous membrane (0.4 μm) on the bottom, immersed in the release medium type III and placed into an orbital shaker set at 37° C. Systems subjected to this test (4 samples for each one) were:
Deg-XG 4 wt %;
Deg-XG 4 wt % loaded with FGF-18 at 540 μg/ml; and
Deg-XG 4 wt % loaded with FGF-18 at 54 μg/ml.
The release medium was changed after 24 hours, 48 hours and then every 3-4 days. The receiving phases collected after 24 hours, 48 hours and 7 days were submitted to Biacore and RP-HPLC analysis.
In Vitro Release Study
The same samples used for swelling tests were also analyzed for the in vitro release tests. In particular, the collected phases were analyzed by HPLC. Selected samples were also analyzed by Biacore (data not shown).

Example 1: Temperature Responsive Gelling Systems Based on DEG-XG

Figure 2:
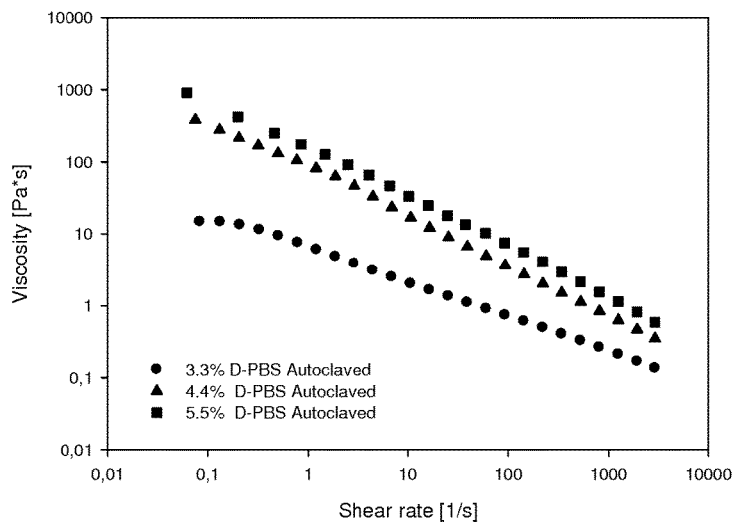
FIG. 2: Shear viscosity vs. shear rate for Deg-XG systems prepared in D-PBS.
Figure 3:
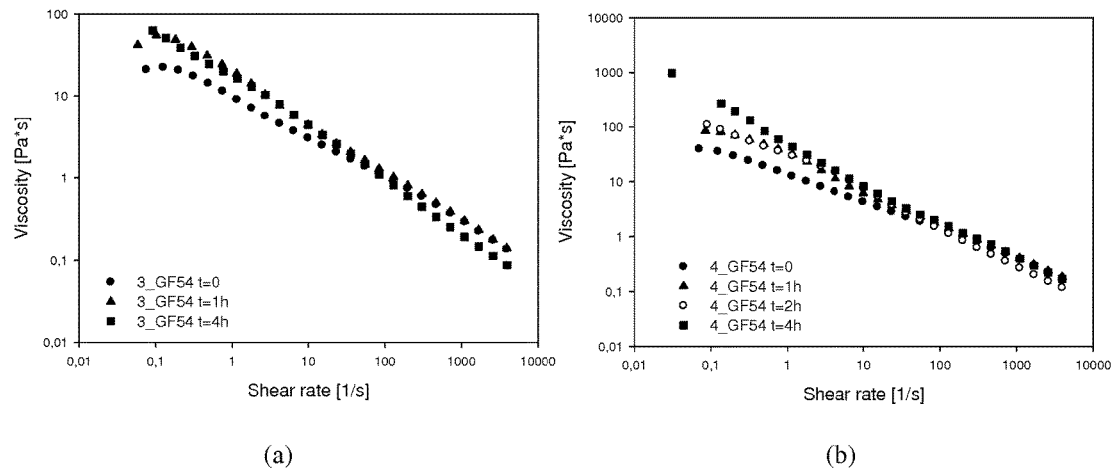
FIG. 3: Shear viscosity measurements for (a) Deg-XG 3 wt % loaded with FGF-18; (b) Deg-XG 4 wt % in D-PBS loaded with FGF-18, after different incubation times at 25° C.
Figure 4:
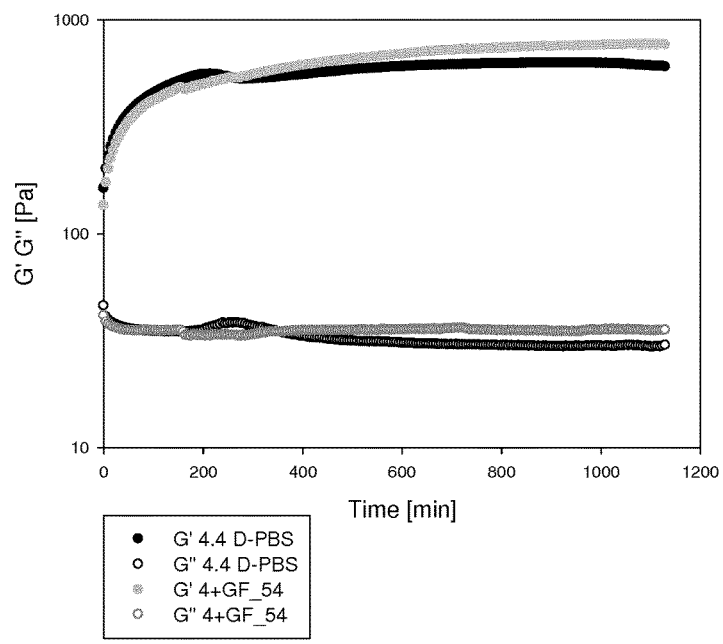
FIG. 4: Time sweep measurements at 25° C. and 1 Hz, for Deg-XG 4.4 wt % and Deg-XG 4 wt % loaded with FGF-18 at 54 mcg/mL in D-PBS.
Figure 5:
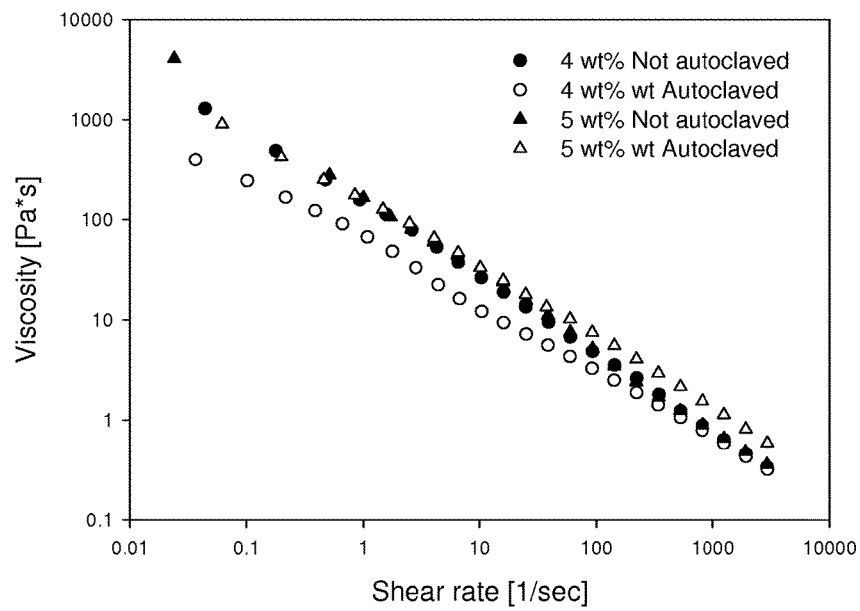
FIG. 5: Autoclaving effect on Deg-XG/water systems (4 and 5 wt %) on shear viscosity.

Deg-XG solutions were prepared in water at 1, 2, 3, 4, 5 wt %. Deg-XG were prepared in D-PBS at 3.3 wt % and 4.4 wt % and they were also loaded with FGF-18 at 54 μg/ml. All systems were subjected to syringability tests after storage at 5° C. overnight (time=0) and after 1, 2 and 3 h of further incubation at 37° C.
Syringability (Tables 1 and 2).
Time to inject a given volume (1 ml) of polymer solution increases with the polymer concentration. The residual amount in the syringe is between 5-8% up to a concentration of 4 wt %, while it increases significantly at about 15% for the 5 wt %. The presence of FGF-18 does not significantly affect the behavior of both systems characterized (3 and 4 wt %). Upon storage at 25° C., the residual amount in the syringe only increases after 4 h for the 3 wt % system, while for the 4 wt % system the residual amount in the syringe increases more markedly with incubation time at 25° C. and injection time is almost doubled after 2 hours. These results suggest that gelation is occurring at 25° C. for both systems and with different kinetics (faster for the higher polymer concentration).
Tilting Behavior (Table 1).
While 4 and 5 Deg-XG wt % became gels before even 5 minutes of incubation at 37° C., the less concentrated solutions became gels not before 30 minutes of incubation. For the 1 wt % no macroscopic gelation was observed.
Shear Viscosity Measurements (Flow Behavior at 25° C.).
Results on the Deg-XG gels as prepared in water and autoclaved are reported in FIG. 1(a-b). Shear viscosity increases with polymer concentration and the non-Newtonian behavior becomes more pronounced.
Shear viscosity versus shear rate for Deg-XG/D-PBS systems (autoclaved) has been checked (FIG. 2). Similarly, shear viscosity increases with polymer concentration and the non-Newtonian behavior becomes more pronounced. Measurements were repeated for the 3 and 4 wt % in the presence of FGF-18 after different incubation times at 25° C.: 1, 2 and 4 hours (FIG. 3). Expectedly, shear viscosity in the low shear rate range progressively increases with incubation time at 25° C. and the slope of the curve increases as well. These results support the hypothesis of a progressive modification of the materials toward gelation already at 25° C.
This behavior is further confirmed by a kinetics study carried out through a time sweep test at fixed frequency of 1 Hz on Deg-XG/D-PBS at 4.4 wt % and loaded with FGF-18 at 54 μg/ml (4 wt %) (FIG. 4).
Influence of Autoclave Treatment.
Deg-XG gels prepared in water at 4 and 5 wt % were subjected to shear viscosity measurements prior and after autoclaving. Autoclaving does not significantly affect the viscosity of 5 wt % solutions (in the investigated shear rate range) while it reduces the shear viscosity at low shear rates for the 4 wt % (FIG. 5). It can be hypothesized that the thermal treatment at 120° C. was beneficial to polymer dissolution in water.

Figure 6:
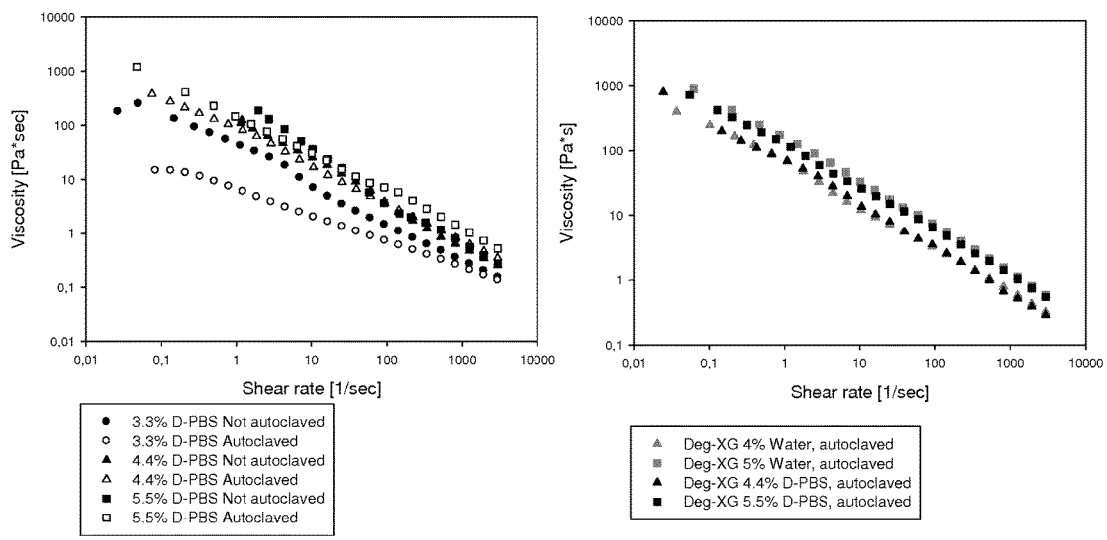
FIG. 6: (a) Autoclaving effect on shear viscosity of Deg-XG/D-PBS systems (3.3, 4.4, 5.5 wt %); (b) Comparison between Deg-XG/Water (4 and 5 wt %) and Deg-XG/D-PBS systems (4.4 and 5.5 wt %, both autoclaved.

For Deg-XG solutions prepared in D-PBS, polymer concentration was incremented by 10% in order to have the same final polymer concentration when these systems are loaded with FGF-18 solutions (polymer/FGF-18 solutions weight ratio=9:1). Autoclaved solutions reveal a slight yellowing, with respect to the ones not autoclaved. Also for these systems the influence of the autoclave treatment is more pronounced at lower concentrations (FIG. 6*a*). Autoclaving in the presence of D-PBS induces a reduction of shear viscosity with respect to similar systems prepared in water (see FIG. 6*b*). In fact, from the figure it is evident that curves referring to 10% more concentrated systems, but autoclaved in the presence of the buffer, superimpose on those of the less concentrated polymer but autoclaved as water solution.

Example 2: Dynamic Mechanical Behavior of Temperature Responsive Gelling Systems Based on DEG-XG The dynamic mechanical behavior of gels incubated at 37° C. for different times was investigated via strain and frequency sweep tests.

Figure 7:
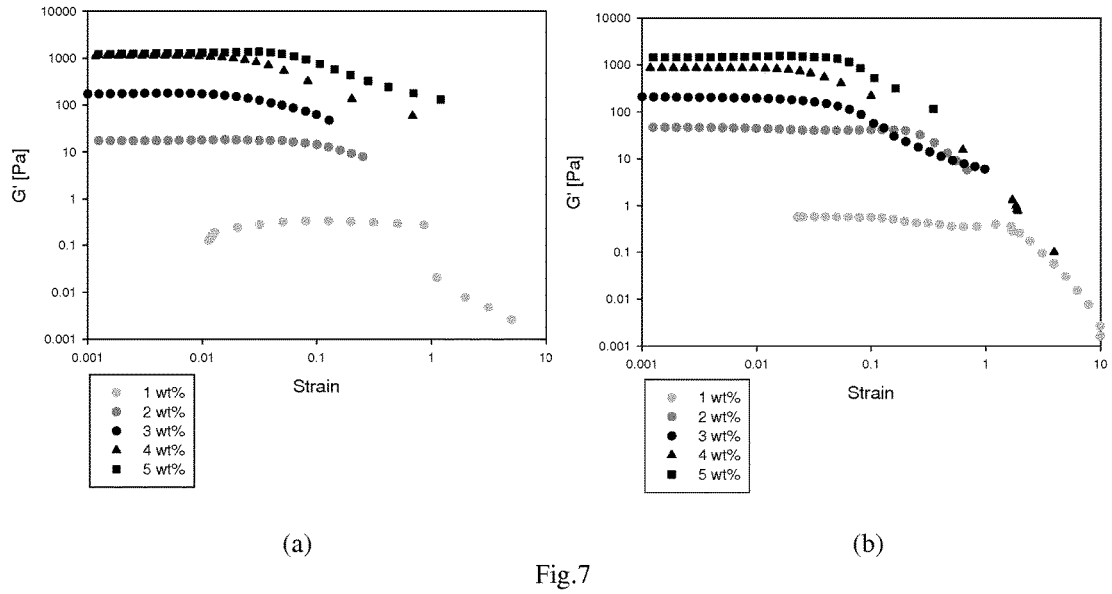
FIG. 7: Strain sweep plots for Deg-XG/water systems (a) after 5 minutes and (b) after 30 minutes of incubation at 37° C.
Figure 8:
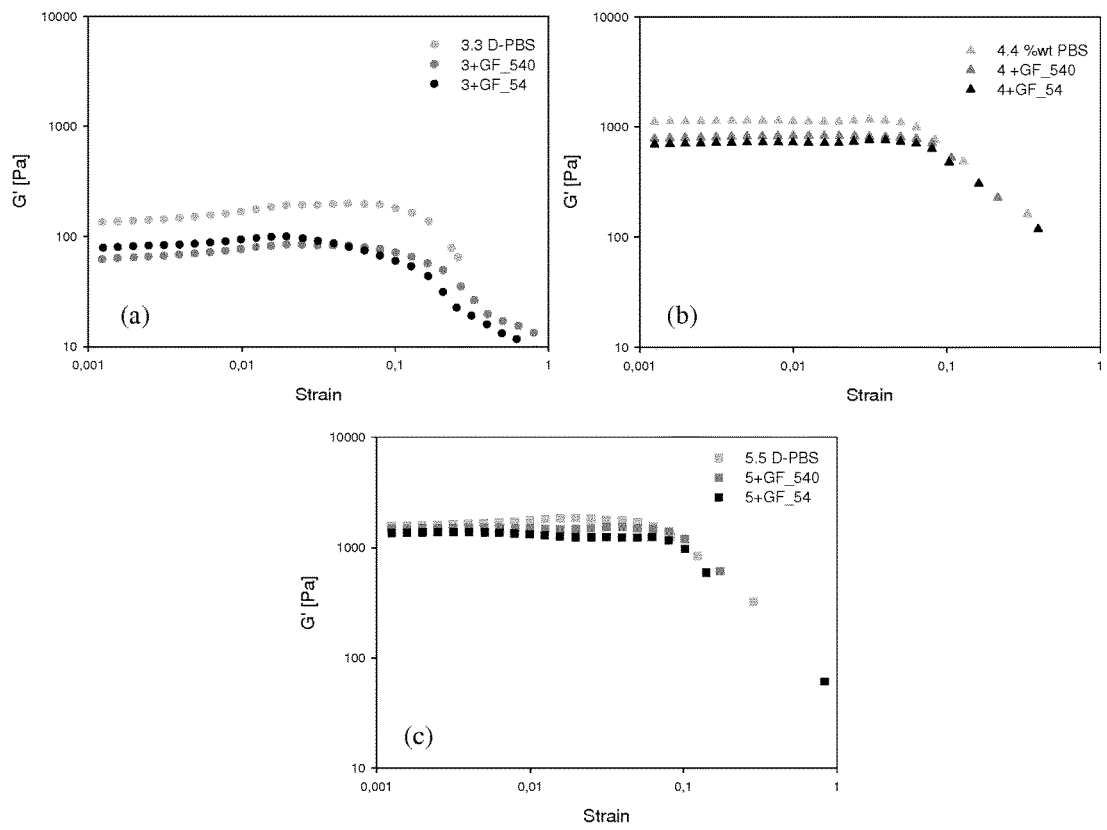
FIG. 8: Strain sweep plots for Deg-XG/D-PBS systems: (a) 3 wt % with and without FGF-18; (b) 4 wt % with and without FGF-18; (c) 5 wt % with and without FGF-18.

G' curves from strain sweeps at 1 Hz frequency for water-based gel systems, after 5 and 30 minutes of incubation at 37° C., are shown in FIG. 7. G' significantly increases with the increase of concentration, although the more elastic-like the material becomes, the lower the strain that it can withstand before losing integrity (condition detected by the abrupt decrease of G'). Strain sweep tests after 30 minutes of conditioning at 37° C. show a general further increase of storage modulus and evidence a difference between the 4 and 5 wt % Deg-XG/water systems. Analogous tests were carried out on D-PBS gels loaded with the GF at 540 and 54 µg/ml and on the "placebo" systems (D-PBS gels without GF) (FIGS. 8*a-c*).

The combined effect of dilution and addition of FGF-18 is in the direction of decreasing G'. The ten-fold more concentrated GF induces only a slight further decrease of G', therefore the observed reduction in G' seems to be mainly attributable to dilution.

Figure 9:
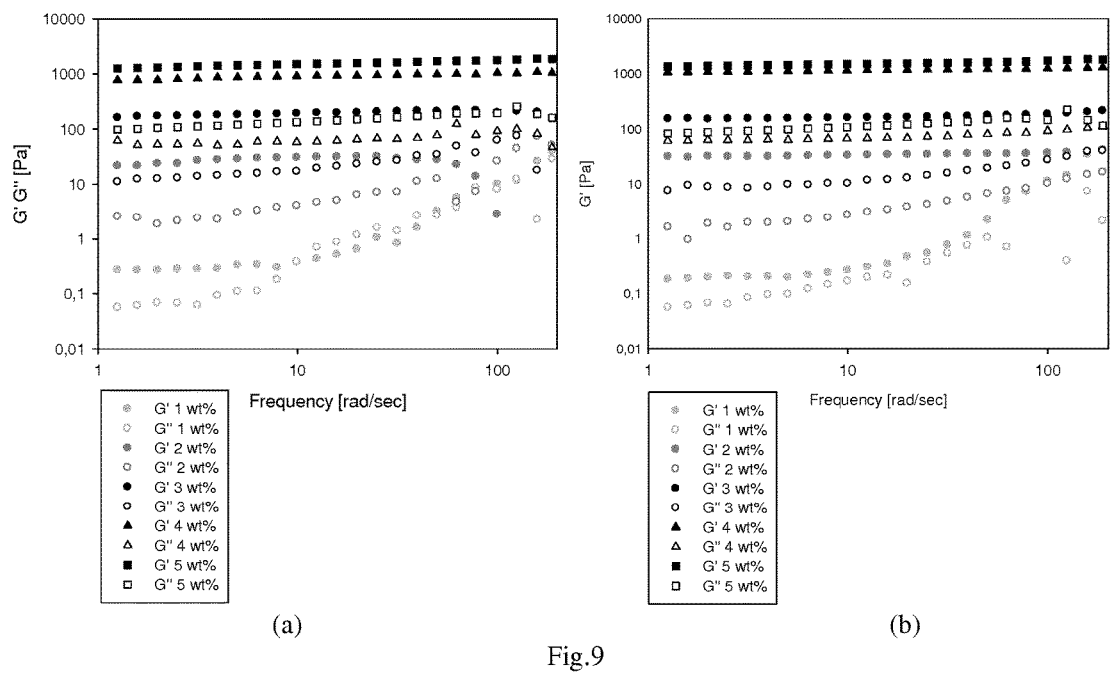
FIG. 9: Frequency sweep plots for Deg-XG/water systems: (a) incubated 5 minutes at 37° C.; (b) incubated 30 minutes at 37° C.

Frequency sweep tests were carried out on all systems at 37° C. In FIG. 9 the G', G" plots for Deg-XG/water systems after 5 minutes or 30 minutes of incubation at 37° C. are shown. All systems, except for the 1 wt %, have G'>G" and G' almost invariant with the frequency. G" becomes invariant with the frequency only for the higher concentrations. Both G' and G" curves increase with polymer concentration.

Figure 10:
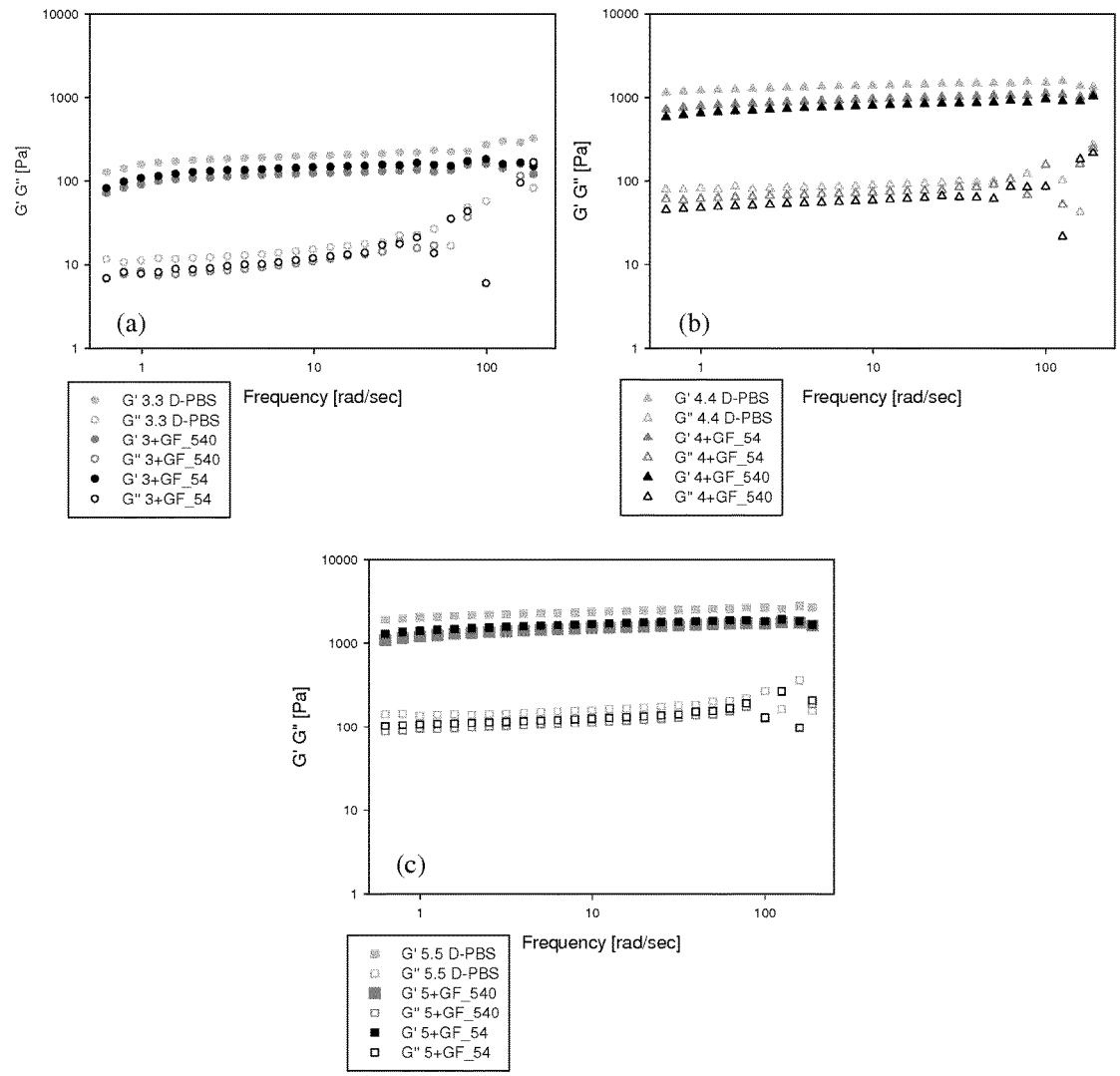
FIG. 10: Frequency sweep plots for Deg-XG/D-PBS systems with (a) 3 wt % with and without FGF-18, (b) 4 wt % with and without FGF-18, and (c) 5 wt % with and without FGF-18.

Frequency sweep tests were also carried out on D-PBS gels loaded with FGF-18 at 540 and 54 µg/mL and on the "placebo" systems (D-PBS gels without FGF-18) (FIGS. 10*a-c*).

These results confirm the already observed decrease of G' when the systems are diluted to be loaded with the GF and no evident effects of the increase of FGF-18 concentration can be appreciated.

Example 3: Gelation Kinetics Study

Figure 11:
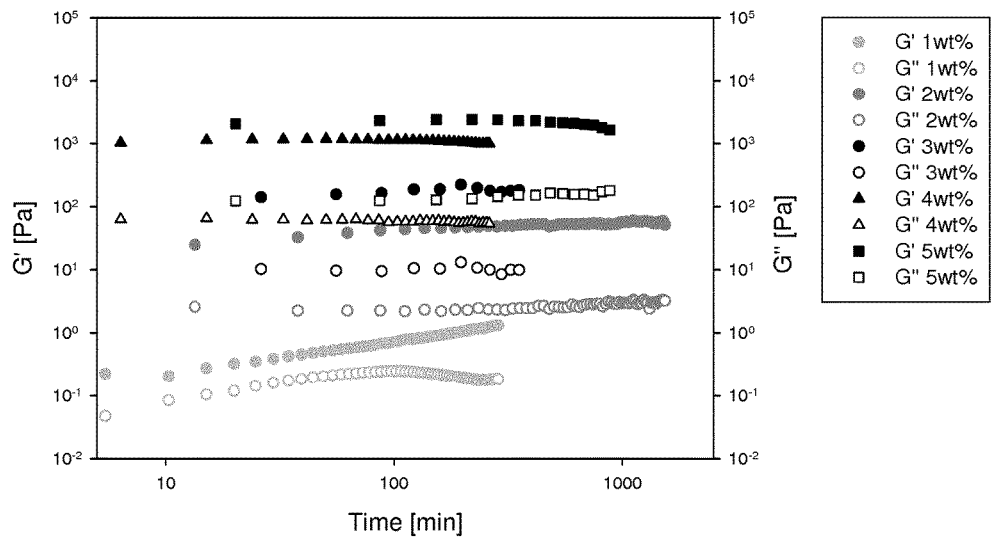
FIG. 11: G' and G" at 1 Hz vs. time for Deg-XG/water systems.

Gelation kinetics study was carried out by repeated frequency sweeps at given time intervals on Deg-XG/water systems at 37° C. Storage modulus and loss modulus values at 1 Hz are plotted as function of time (FIG. 11).

While the 1 wt % Deg-XG system shows a steady increase with time of G' and G", which first increase and then decrease, all the other systems show almost constant values of both components of the complex modulus in the time frame investigated. These results are also in good agreement with the qualitative preliminary investigation of flow behavior with tilting tests.

In light of the observed similarities between D-PBS and water systems, we can assume that the two type of gels have the same qualitative behavior.

Example 4: Freezing-Thawing and Lyophilization Effects

Figure 12:
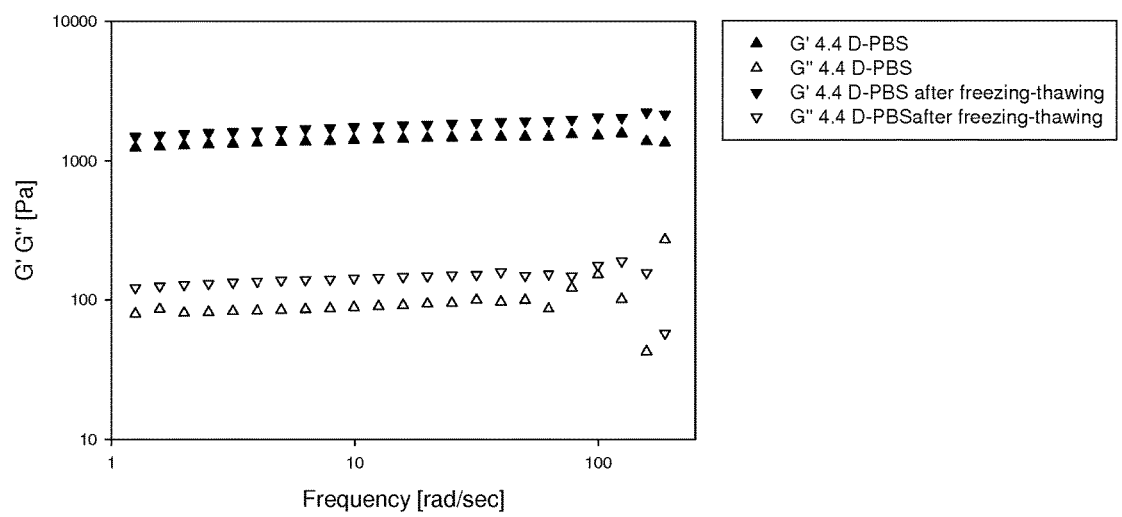
FIG. 12: Freezing-thawing effect on Deg-XG/D-PBS 4.4 wt % system.
Figure 13:
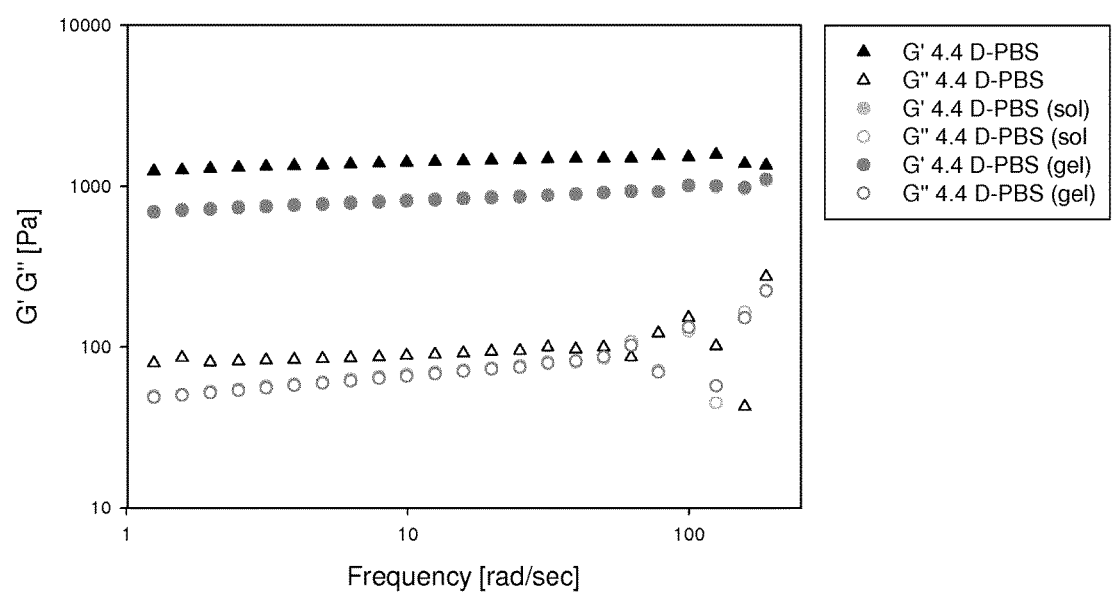
FIG. 13: Lyophilized and reconstituted Deg-XG 4.4 wt % in D-PBS, in both sol and gel form.
Figure 14:
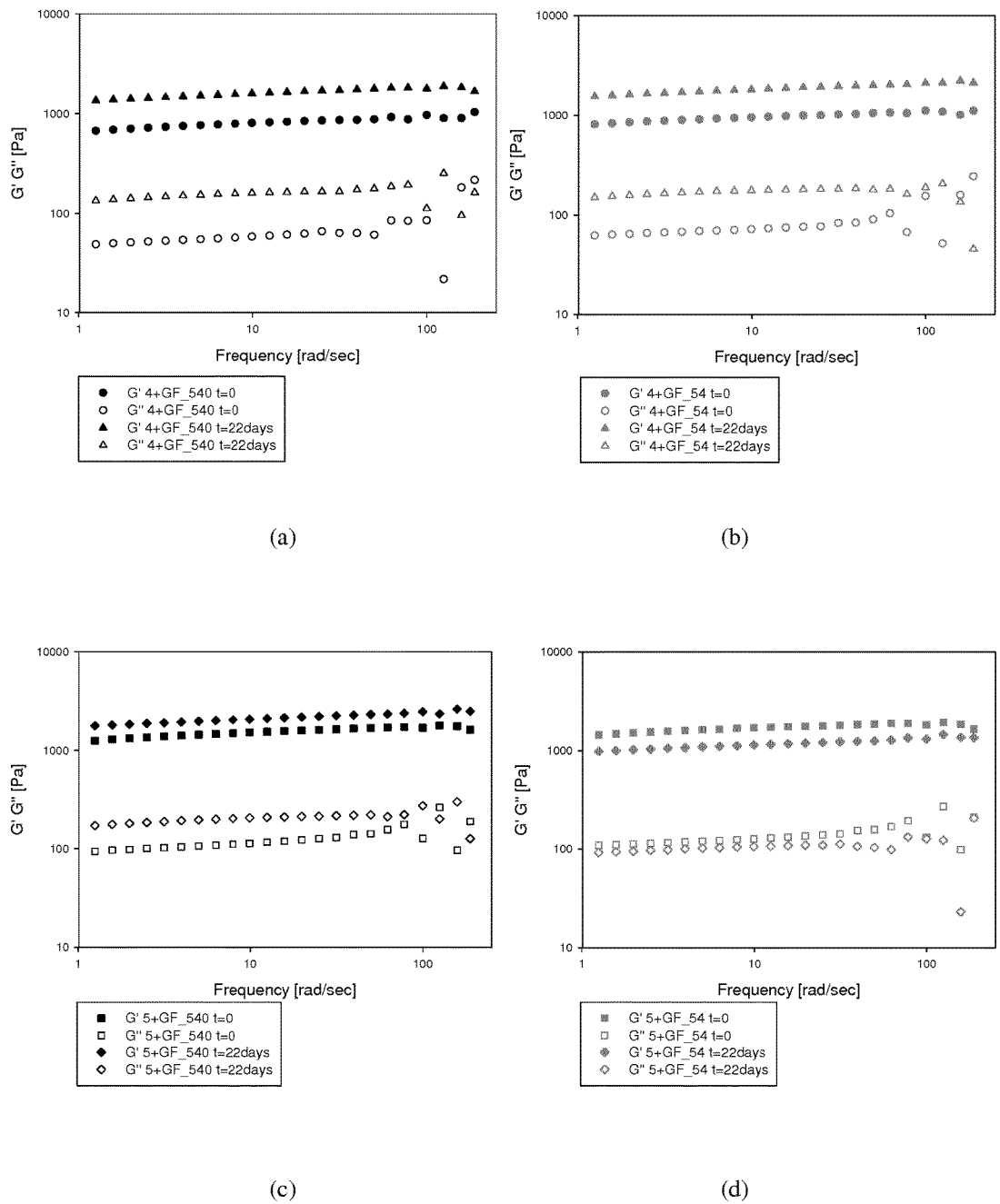
FIG. 14: Frequency sweep plots for fresh and eroded samples: (a) Deg-XG 4 wt % loaded with FGF-18 at 540 μm/ml; (b) Deg-XG 4 wt % loaded with FGF-18 at 54 μm/ml; (c) Deg-XG 5 wt % loaded with FGF-18 at 540 μm/ml; (d) Deg-XG 5 wt % loaded with FGF-18 at 54 μm/ml.

In order to gather some information on possible storage conditions for Deg-XG gels, on the system at 4.4 wt % prepared in D-PBS the effect of one freeze-thaw cycle on the dynamic mechanical spectrum was investigated. For the same purpose, the effects of lyophilization and reconstitution were evaluated. In this last case the material was freeze-dried from both the sol (at the storage temperature of 5° C.) and the gel states (after conditioning at 37° C.) (FIGS. 12 and 13).

Both G' and G" increase after freeze-thawing, while the effect of lyophilization and reconstitution in D-PBS at 5° C. overnight without stirring is in the direction of a decrease of both G' and G", regardless of the initial state of the material. Both these results evidence that processes that favor Deg-XG dissolution lead to stronger gels, whereas processes that favor Deg-XG aggregation reduce the gel strength. Deg-XG dissolution in the aqueous medium is a critical parameter for the quality of network formed at 37° C.

Example 5: Scanning Electron Microscopy of Freeze Dried Gels

Deg-XG gels prepared in water, quickly frozen by immersing them in liquid nitrogen (inside a vial) and freeze-dried were analyzed by Scanning Electron Microscopy (data not shown). All systems show irregular porosity, with larger cavities of tens of microns and smaller pores of only few microns. The prevailing effect of increasing the concentration of polymer is reducing the dimensions of the larger cavities. But despite of the inherent heterogeneity, the samples' morphology was quite uniform.

Example 6: Swelling-Erosion Studies

A preliminary study of the swelling-erosion behavior of Deg-XG/water gels at 4 wt % and 5 wt % was performed over a time scale of 60 days. Gel samples were weighed before and during incubation at 37° C. Ws(t) is the weight of the swollen sample at time t and Ws(0) is the weight of the sample at time t=0 (Table 3). After 60 days the test was stopped due to mold growth. For both systems, Ws(t)/Ws(0) [%] slowly decreases with time. Eroded gels were subjected to SEM microscopy after being quickly frozen in liquid nitrogen and freeze-dried (data not shown). After erosion the gel structure does not collapse and the porosity becomes more homogeneous. Furthermore, porosity appears more open and interconnected for the 4 wt % than for the 5 wt % system.

Swelling-erosion experiments were repeated for Deg-XG/D-PBS gels at 4 and 5 wt % loaded with FGF-18 at 540 µg/ml and 54 µg/ml (Table 4). For each system Ws(t)/Ws(0)

[%] slowly decreases with time, and comparatively more and more rapidly with respect to the systems produced in water. This may be either a direct effect of the PBS salts or, more likely, an indirect effect of PBS affecting the polymer's molecular structure upon autoclaving. After 22 days of dwelling in the release medium, the eroded gels were subjected to frequency sweep tests in order to evaluate their mechanical properties (FIGS. 14a-d).

After 22 days of immersion in the release medium the residual gels generally exhibited higher storage modulus G' and loss modulus G" values, thus suggesting a rearrangement of the network toward a stronger structure, which is concomitant to the erosion of the less cross-linked portions of the material. Only Deg-XG 5 wt % loaded with FGF-18 at 54 µg/ml showed an opposite trend.

Example 7: Study of Gel Erosion/Protein Release

The study was performed on 4 wt % Deg-XG prepared in PBS at pH 7.3. The receiving phases collected after 24 hours, 48 hours and 7 days were submitted to Biacore and RP-HPLC analysis (data not shown). RP-HPLC analysis did not reveal distinct chromatographic peaks attributable to a burst release of FGF-18. The same receiving phases were also subjected to Biacore analysis. Similarly, no FGF-18 was detected. This suggests that protein is entrapped in the gel matrix for the observation period.

Figure 15:
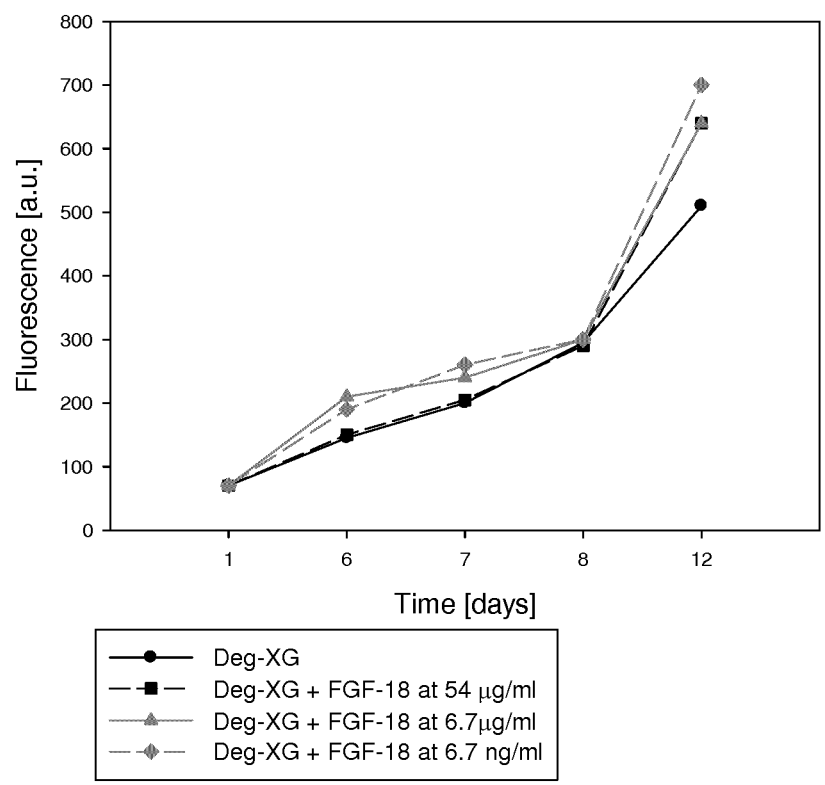
FIG. 15: Cell proliferation assay by Alamar Blue reagent (X-axis: incubation time (days). Y-axis: cell viability). It shows the results of the Alamar Blue assay (5000 chondrocytes/wells) for cell proliferation carried out with chondrocytes cultured on Deg-XG hydrogel (at 3.3 wt %) samples, either unloaded (control) or loaded with FGF-18 at three different concentrations: 54 mcg/ml, 6.7 mcg/ml, 6.7 ng/ml.

Example 8: Cell Proliferation Assay 8.1. Alamar Blue Assay for Cell Proliferation Alamar Blue assay (5000 chondrocytes/wells) for cell proliferation was carried out with chondrocytes cultured on Deg-XG hydrogel (at 3.3 wt %), either unloaded (control) or loaded with FGF-18 at three different concentrations: 54 mcg/ml, 6.7 mcg/ml, and 6.7 ng/ml. All systems including the control system (Deg-XG gel without FGF-18) showed significant cell proliferation over time (see FIG. 15). The presence of the growth factor did not affect the proliferation rate during the first eight days, while it slightly increased it for prolonged incubation times. No influence of FGF-18 concentration was observed in the investigated concentration range for the growth factor.

8.2. Acridine Orange Staining for Apoptosis Evaluation

Figure 16:
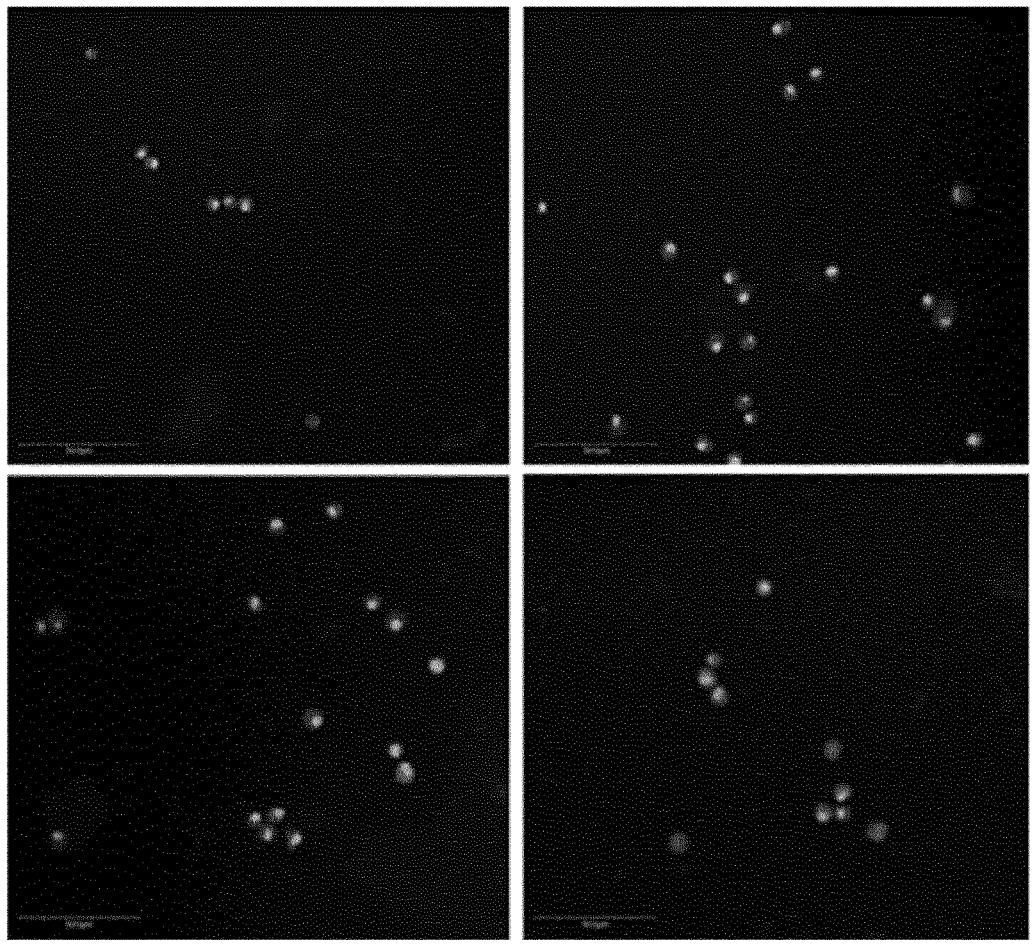
FIG. 16: Acridine orange staining of chondrocytes cultured for 12 days on Deg-XG (top left); Deg-XG+FGF-18 at 6.7 ng/ml (top right); Deg-XG+FGF-18 at 6.7 ug/ml (bottom left); and Deg-XG+FGF-18 at 54 ug/ml (bottom right).

Confocal microscopy analysis was carried out on cells cultured for 12 days on FGF-18 loaded and unloaded Deg-XG hydrogels after staining with Acridine Orange. Acridine Orange is a cell-permeating nucleic acid-binding dye that emits green fluorescence when bound to double-strand DNA and red fluorescence when bound to single-strand DNA or RNA. This staining discriminates between living (green nuclei) and apoptotic (red nuclei) cells. As shown in FIG. 16, the green color and round-shaped nuclei indicate that cells did not undergo DNA damage in both the presence and the absence of FGF-18.

8.3. Optical Microscopy Study as Function of the Incubation Time and FGF-18 Loading Content Chondrocyte proliferation on FGF-18 loaded and unloaded Deg-XG gels was followed under a light microscope over a length time of 7 days. Loading content for the growth factor ranged from 6.7 ng/ml to 54 ug/ml. It was observed that in all systems chondrocytes initially formed clusters. When gels were loaded with FGF-18 at lower concentrations (6.7 ng/ml and 6.7 mcg/ml), after 48 h of incubation chondrocytes moved away from the clusters, colonizing other portions of the scaffold (data not shown).

8.4. Cell Invasion Studies Through Confocal Microscopy.

Confocal microscopy analysis of different sections taken from a 210 µm thick layer of a hydrogel sample of about 2 mm overall thickness was carried out for the Deg-Xg+FGF 6.7 mcg system after for 4 days of incubation. Cells were stained with ethidium bromide (red). The results show the presence of chondrocytes across the thickness of the material. Since cell seeding was performed on the hydrogel surface, the presence of cells in different positions across the thickness suggests that proliferating cells may access the inner layers of the gels (data not shown).

Example 9: Preparation of Chitosan Gels 9.1. Generalities

For the screening of chitosan formulations, the preparation of the polymer liquid solutions made use of three different chitosans: 95% deacetylation degree (DD) with high molecular weight (HMW), 95% DD with low MW (LMW) and 75% DD with high MW (HMW). Polymer liquid solutions were prepared by gradually adding the chitosan to a solution of acetic acid 0.1 N under vigorous stirring at either 5° C. or 25° C. The amount of polymer was calculated to have a final polymer concentration in the polymer liquid solution of 1% wt, 1.5% wt or 2% wt. Once the chitosan was completely solubilized, a solution of $KH_2PO_4$ at a concentration of 10 mM, 100 mM or 500 mM in Milli-Q water was added under stirring, to have a final concentration in the polymer liquid solution of either 1 mM, 10 mM or 50 mM. Finally, a solution of β-glycerophosphate (β-GP) at a concentration of 20% wt in Milli-Q water was added in order to adjust the pH of the final liquid solution to a value of either 6.0, 6.5 or 7.0. The final concentration of β-GP in the polymer liquid solution ranged from 0.5% wt to 7% wt for the accepted formulations. It was not always possible to reach the desired pH value as too high an amount of β-GP was necessary, exceeding the target osmolality value of 350 mOsm/Kg or obtaining a gel already at room temperature. The polymer liquid solutions, when applicable, were then incubated at 37° C. up to gel formation. The osmolality of all the screened formulations was measured, discarding the formulations with an osmolality higher than 350 mOsm/Kg, i.e., formulations with final β-GP concentrations higher than 2.5% wt.

9.2. Preliminary Screening of Placebo Formulations (See Table 5)

Chitosan is reported to be able to undergo sol-gel transitions with temperature changes, but the process is highly influenced by the polymer molecular weight (MW), its deacetylation degree (DD), polymer concentration in solution, temperature, time and speed of mixing during the solubilization of the polymer, final pH of the solution and the presence of other excipients.

Therefore, an exhaustive screening of the different possible combinations was required. It is noteworthy that chitosan can be solubilized in water only at acidic pH. An increase in pH causes its aggregation and precipitation. A way to overcome this issue is the use of β-GP to increase the pH while maintaining the chitosan in solution.

The study was focused at the beginning on HMW chitosan with 75% DD. Several polymer liquid solutions were prepared in hydrochloric acid 0.1 N, differing in final chitosan concentration from 1% wt to 2.5% wt and final β-GP concentration from 1.6% wt to 50% wt (1.6, 5, 5.6, 8, 30, 50%), and having different excipients, namely gelatine, glucosamine, hyaluronic acid, hydroxyethyl cellulose, carboxymethyl cellulose, trehalose, and different final pH values, from 6.0 to 7.0. These excipients were reported to play a role in the induction of gel formation (Cheng et al., 2010; Schuetz et al., 2008; Yan et al., 2010).

Only one of the screened formulations was able to form a gel at 37° C. after 5 minutes of incubation at 37° C., but the amount of β-GP was higher than 8% wt, reported in the literature as the limit above which cytotoxicity is recorded (Ahmadi et al., 2008). Therefore, all the following formulations were prepared considering that limitation. The screening continued, moving to a chitosan having a higher DD value. The first trials were based on LMW chitosan with 95% DD. The polymer solutions were prepared always in hydrochloric acid 0.1 N, solving the polymer under vigorous stirring at either 5° C. or 25° C.

After complete solubilization of the polymer, the other excipients were added, adding β-GP only at the end. β-GP was responsible for the increase in the pH value then, promoting the gelation process. The first trials were focused on formulations based only on chitosan and β-GP at different combinations of relative concentrations. It was observed that using high concentrations of chitosan (2% or 3% wt) and high concentrations of β-GP (8% wt), the formation of the gel occurred already at room temperature, and in some cases also at 5° C.

Decreasing the concentrations of either component, the formulation remained liquid, also after long incubation at 37° C. Only in one case was the formation of the gel registered, but after 2 hours of incubation at 37° C., this was too long a time for the purpose of this study. Therefore, the addition of an excipient was mandatory for improving the formulation. Hydroxyethyl cellulose (HEC) was selected as the most appropriate excipient and a further screening was carried out. During this evaluation, chitosan concentration ranged from 1.5% wt to 2% wt and starting HEC concentration was 0.5% wt, but in these conditions, the polymer solution became a gel even at room temperature during the addition of β-GP, if its concentration was above 1.8% wt. A liquid solution able to become a gel at 37° C. after 13 minutes of incubation was obtained with the following composition: 1.5% wt of chitosan, 0.5% wt of HEC and 1.7% wt of β-GP.

9.3. Optimization of the Formulation (See Table 5)

In the attempt to improve this formulation, the following trials were made, maintaining the concentration of β-GP almost constant at the value of 1.65-1.7% wt. Chitosan concentration varied from 1.5% wt to 1.8% wt and the amount of HEC was gradually decreased to 0.1% wt.

Several candidate formulations were selected with this strategy. However, the investigation did not continue in this direction, as it was found that HEC excipient can contain a contaminant reported to be cytotoxic and, on the other hand, responsible for the gelation process modulation in the presence of chitosan (Hoemann et al., 2007). Other excipients tested in the previous experiments, such as gelatine or glucosamine, did not give positive results.

A final screening work was then started, using three kinds of chitosan polymer, differing in molecular weight and DD: HMW chitosan with 75% DD, HMW chitosan with 95% DD and LMW chitosan with 95% DD. The work was also planned on LMW chitosan with 85% DD, but the material was not available before the end of the study. In that work each chitosan was tested at three fixed concentrations, 1, 1.5 and 2% wt, and the polymer solutions were prepared in order to have final pH values of 6.0, 6.5 and 7.0. In order to reduce the amount of β-GP used to increase the pH value of the solution, the polymer was solved in acetic acid 0.1 N, instead of the HCl 0.1 N used in the previous experiments. The osmolality of the final solution was also monitored and kept below the value of ~350 mOsm/kg. Thus, the formulations that required too high an amount of β-GP to reach the desired pH, also leading to too high an osmolality value, were discarded. In these screening tests, the contribution of ionic strength was also studied, as it was reported that the presence of salts could give a positive contribution to the gelation process (Filion et al., 2007).

As sodium salts had to be avoided for possible interactions with the protein, $KH_2PO_4$ was chosen and added to the polymer solution at the final concentration of 1 mM, 10 mM or 50 mM. Chitosan with 75% DD gave no positive results and it was completely abandoned. Neither HMW chitosan with 95% DD gave positive results: chitosan concentrations higher than 1% wt required too high an amount of β-GP to reach the fixed pH values, exceeding the target osmolality value, and the formulations at 1% wt were not able to form a gel at 37° C. Two candidate formulations were selected with LMW chitosan having 95% DD, as they underwent sol-gel transition at 37° C., but the preparation of these polymer solutions was not completely reproducible. Indeed, it was observed that the time required to obtain a gel and the physical macroscopic characteristics of the polymer liquid solutions changed significantly, depending on the time spent to dissolve the polymer, the speed of mixing during the polymer dissolution and during the mixing of the excipients, and, finally, the temperature and volume of the prepared solution.

This high variability of the results led to the decision to interrupt the study on this polymer.

TABLE 1

Syringability and tilting behaviour tests data for Deg-XG/water systems

| | Syringability | | Tilting behaviour | | | |
|---|---|---|---|---|---|---|
| Concentration | Injection time | Residual amount in the | | | | |
| (wt %) | (sec/mL) | syringe (%) | 5 min | 30 min | 60 min | 24 hrs |
| 1 | 3.5 | 6.8 | Flow | Flow | Flow | Flow |
| 2 | 5.5 | 5.1 | Flow | No flow | No flow | No flow |
| 3 | 9.4 | 5.5 | Flow | No flow | No flow | No flow |
| 4 | 14.7 | 7.9 | No flow | No flow | No flow | No flow |
| 5 | 15.2 | 15.6 | No flow | No flow | No flow | No flow |

TABLE 2

Syringability data for Deg-XG 3 wt % and 4 wt % loaded with FGF-18 at 54 mcg/mL

| System | Incubation time at 25° C. (hr) | Injection time (sec/mL) | Residual amount in the syringe (%) |
|---|---|---|---|
| Deg-XG 3 wt % + FGF-18 (54 mcg/mL) | 0 | 11.6 | 5.5 |
|  | 1 | 10.7 | 7.2 |
|  | 2 | 13.0 | 7.3 |
|  | 4 | 11.1 | 8.1 |
| Deg-XG 4 wt % + FGF-18 (54 mcg/mL) | 0 | 13.2 | 6.4 |
|  | 1 | 10.9 | 6.6 |
|  | 2 | 19.5 | 9.7 |
|  | 4 | 18.7 | 12.3 |

TABLE 3

Swelling erosion data for Deg-XG systems prepared in water

| | ws(t)/Ws0 (%) | | | | | |
|---|---|---|---|---|---|---|
| System | 1 day | 19 days | 27 days | 34 days | 45 days | 59 days |
| Deg-XG 4 wt % H$_2$O | 106.6 | 90.1 | 80.7 | 78.8 | 75.8 | 71 |
| Deg-XG 5 wt % H$_2$O | 96.4 | 86 | 78.5 | 75.8 | 69.8 | 66.2 |

TABLE 4

Swelling erosion data for Deg-XG systems loaded with FGF-18 at 54 mcg/mL (autoclaved)

| | ws(t)/ws0 (%) | | | | | |
|---|---|---|---|---|---|---|
| System | 5 day | 9 days | 14 days | 16 days | 19 days | 22 days |
| Deg-XG 4 wt % + FGF18 540 mcg/mL | 85.2 | 80.5 | 79.2 | 75.7 | 75 | 71.6 |
| Deg-XG 5 wt % + FGF18 540 mcg/mL | 84.8 | 81.3 | 80.5 | 78.1 | 75.1 | 74.8 |
| Deg-XG 4 wt % + FGF18 54 mcg/mL | 79.7 | 78.3 | 76.3 | 73.3 | 72.5 | 70.3 |
| Deg-XG 5 wt % + FGF18 54 mcg/mL | 84.3 | 78.5 | 78.5 | 77 | 76.6 | 74.7 |

TABLE 5

Gelation time at 37° C. of selected chitosan-based formulations

| Formulation | Chitosan MW and DD | Chitosan (% wt) | B-GP (% wt) | HEC (% wt) | KH2PO4 (mM) | pH | Osmolality (mOsm/kg) | Gelation time |
|---|---|---|---|---|---|---|---|---|
| I | HMW 75% | 1.8 | 50 | / | / | / | / | 5 min |
| II | HMW 75% | 2 | 6.9 | / | / | 7.2 | / | 2 h |
| III | HMW 75% | 2 | 1.2 | 0.5 | / | 6.1 | / | 25 min |
| IV | HMW 75% | 1.5 | 1.7 | 0.5 | / | 6.1 | / | 13 min |
| V | HMW 75% | 1.5 | 1.6 | 0.25 | / | 6.2 | / | 19 min |
| VI | HMW 75% | 1.6 | 1.6 | 0.25 | / | 6.3 | / | 30 min |
| VII | HMW 75% | 1.8 | 1.5 | 0.5 | / | 6.3 | / | 12 min |
| VIII | HMW 75% | 1.8 | 1.7 | 0.1 | / | 6.4 | / | 50 min |
| IX | HMW 95% | 1.0 | 2.5 | / | 0 | 6.8 | 384 | 24 h |
| X | LMW 75% | 2.0 | 2.1 | / | 10 | 7.0 | 346 | 3 h |
| XI | LMW 75% | 2.0 | 2.5 | / | 10 | 6.9 | 379 | 2 h |

REFERENCES

1. Ellsworth et al., 2002, Osteoarthritis and Cartilage, 10: 308-320
2. Shimoaka et al., 2002, JBC 277(9):7493-7500
3. WO2008/023063
4. WO2004/032849
5. WO2012/172072
6. J. Ringe et al., 2012, "Regenerative medicine in rheumatic disease-progress in tissue engineering," Nature Reviews Rheumatology, 8(8):493-498
7. J. K. Tessmar, A. M. Göpferich, 2007, "Matrices and scaffolds for protein delivery in tissue engineering", Adv. Drug Delivery Rev., 59:274-291
8. C. Lo Presti et al., 2011, "Pulsatile protein release and protection using radiation-crosslinked polypeptide hydrogel delivery devices," Reactive & Functional Polymers, 71:155-167

9. WO2008/063418
10. C. Dispenza et al., 2011, "E-beam irradiation and UV photocrosslinking of microemulsion-laden poly(N-vinyl-2-pyrrolidone) hydrogels for "in situ" encapsulation of volatile hydrophobic compounds", Polym. Chem., 2:192
11. Rilton et al., 2011, "Degalatosylation of xyloglucan: effect on aggregation and conformation, as determined by time dependant static light scattering HPSEC-MALLS and viscosimetry". Carbohydrate Polymers, 83:1636-1642
12. Shirakawa et al., 1998, "Tailoring of xyloglucan properties using an enzyme," Food Hydrocolloids, 12:25-28.
13. WO98/16644
14. WO2006/063362
15. Custers et al., 2007, Osteoarthritis and Cartilage, 15:1241-1248
16. Cheng et al., 2010, Tissue Engineering 16A:695-703
17. Schuetz et al., 2008, Eur. J. Pharm. Biopharm., 68:19-25
18. Yan et al., 2010, J. Biomat. Appl., 24:625-637
19. Ahmadi et al., 2008, J. Biomed. Mater. Res., 86A:824-832
20. Hoemann et al., 2007, J. Biomed. Mater Res., 83A:521-529
21. Filion et al. 2007, Biomacromol., 8:3224-3234

The invention claimed is:

1. A liquid formulation comprising FGF-18, a xyloglucan and a buffer keeping the pH between about 5.5 and about 6.0, wherein said xyloglucan is partially degalactosylated and wherein FGF-18 is selected from the group consisting of:
   a) a polypeptide comprising amino acid residues 28-207 of SEQ ID NO:1,
   b) a polypeptide comprising amino acid residues 28-196 of SEQ ID NO:1, and
   c) a polypeptide comprising SEQ ID NO:2.

2. The liquid formulation according to claim 1, wherein said xyloglucan has a degalactosylation degree at or about 44 or 45%.

3. The liquid formulation according to claim 1, wherein the buffer is a phosphate buffer.

4. The liquid formulation according to claim 1, wherein FGF-18 is in a concentration of 0.00001 to 0.6% wt, the xyloglucan is in a concentration of 3 to 4% wt and the buffer is in a concentration of 96 or 97% wt.

5. The liquid formulation according to claim 1, wherein the ratio of xyloglucan:FGF-18 is 9:1.

6. A method for producing a hydrogel comprising the steps of:
   a) preparing a liquid formulation according to claim 1, and
   b) exposing the liquid formulation at a temperature of 37° C. or about 37° C. to form the hydrogel.

7. The method according to claim 6, wherein the hydrogel is formed after the liquid formulation is administered to a subject and the liquid formulation is exposed to a temperature of 37° C. or about 37° C. in said subject.

8. A hydrogel obtained according to the method of claim 6.

9. An article of manufacture comprising a container containing the liquid formulation according to claim 1.

10. A method of improving cartilage repair or treating a cartilage disorder in a subject, the method comprising the steps of:
    a) preparing a liquid formulation according to claim 1, and
    b) intraarticularly administering the liquid formulation prepared in step a) into the subject.

11. The method according to claim 10, wherein the cartilage disorder is osteoarthritis or cartilage injury.

* * * * *

UNITED STATES PATENT AND TRADEMARK OFFICE
CERTIFICATE OF CORRECTION

PATENT NO. : 10,293,051 B2  
APPLICATION NO. : 15/105622  
DATED : May 21, 2019  
INVENTOR(S) : Caterina Lo Presti, Donatella Bulone and Clelia Dispenza Page 1 of 1

It is certified that error appears in the above-identified patent and that said Letters Patent is hereby corrected as shown below:

On the Title Page

(30) Foreign Application Priority Data:
"Dec. 23, 2014" should read --Dec. 24, 2013--.

Signed and Sealed this
Twenty-sixth Day of November, 2019

Andrei Iancu
*Director of the United States Patent and Trademark Office*

SEQUENCE LISTING

<160> NUMBER OF SEQ ID NOS: 2

<210> SEQ ID NO 1
<211> LENGTH: 207
<212> TYPE: PRT
<213> ORGANISM: Homo sapiens
<220> FEATURE:
<223> OTHER INFORMATION: human FGF-18

<400> SEQUENCE: 1

```
Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
                20                  25                  30

Phe Arg Ile His Val Glu Asn Gln Thr Arg Ala Arg Asp Asp Val Ser
            35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205
```

<210> SEQ ID NO 2
<211> LENGTH: 170
<212> TYPE: PRT
<213> ORGANISM: Artificial
<220> FEATURE:
<223> OTHER INFORMATION: recombinant truncated FGF-18(sprifermin)

<400> SEQUENCE: 2

```
Met Glu Glu Asn Val Asp Phe Arg Ile His Val Glu Asn Gln Thr Arg
```

-continued

```
1               5                   10                  15
Ala Arg Asp Asp Val Ser Arg Lys Gln Leu Arg Leu Tyr Gln Leu Tyr
            20                  25                  30

Ser Arg Thr Ser Gly Lys His Ile Gln Val Leu Gly Arg Arg Ile Ser
            35                  40                  45

Ala Arg Gly Glu Asp Gly Asp Lys Tyr Ala Gln Leu Leu Val Glu Thr
        50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

Thr Ser Lys Glu Cys Val Phe Ile Glu Lys Val Leu Glu Asn Asn Tyr
            100                 105                 110

Thr Ala Leu Met Ser Ala Lys Tyr Ser Gly Trp Tyr Val Gly Phe Thr
            115                 120                 125

Lys Lys Gly Arg Pro Arg Lys Gly Pro Lys Thr Arg Glu Asn Gln Gln
    130                 135                 140

Asp Val His Phe Met Lys Arg Tyr Pro Lys Gly Gln Pro Glu Leu Gln
145                 150                 155                 160

Lys Pro Phe Lys Tyr Thr Thr Val Thr Lys
                165                 170
```